United States Patent
Masunishi et al.

(10) Patent No.: US 9,829,398 B2
(45) Date of Patent: Nov. 28, 2017

(54) PRESSURE SENSOR, MICROPHONE, ULTRASONIC SENSOR, BLOOD PRESSURE SENSOR, AND TOUCH PANEL

(71) Applicant: KABUSHIKI KAISHA TOSHIBA, Minato-ku, Tokyo (JP)

(72) Inventors: Kei Masunishi, Kanagawa (JP); Hideaki Fukuzawa, Kanagawa (JP); Yoshihiko Fuji, Kanagawa (JP); Akiko Yuzawa, Kanagawa (JP); Kazuaki Okamoto, Tokyo (JP)

(73) Assignee: Kabushiki Kaisha Toshiba, Tokyo (JP)

(*) Notice: Subject to any disclaimer, the term of this patent is extended or adjusted under 35 U.S.C. 154(b) by 203 days.

(21) Appl. No.: 14/721,497

(22) Filed: May 26, 2015

(65) Prior Publication Data
US 2015/0338293 A1   Nov. 26, 2015

(30) Foreign Application Priority Data

May 26, 2014 (JP) ................. 2014-108502

(51) Int. Cl.
*G01H 11/00* (2006.01)
*G01L 1/22* (2006.01)
(Continued)

(52) U.S. Cl.
CPC ............... *G01L 1/22* (2013.01); *A61B 5/021* (2013.01); *A61B 5/02141* (2013.01); *A61B 5/05* (2013.01);
(Continued)

(58) Field of Classification Search
CPC . G01L 1/22; G01L 9/007; G01L 1/125; A61B 5/02141; A61B 2562/028; A61B 2562/0204
See application file for complete search history.

(56) References Cited

U.S. PATENT DOCUMENTS 4,217,783 A * 8/1980 Ito ............................. G01L 9/16
338/32 R
5,107,710 A * 4/1992 Huck ...................... G01L 9/065
338/4
(Continued)

FOREIGN PATENT DOCUMENTS

EP    2 184 576 A1   5/2010
JP    2007-139517    6/2007
(Continued)

OTHER PUBLICATIONS

Dehé, "Silicon microphone development and application," Sensors and Actuators (2007), pp. 283-287.
(Continued)

*Primary Examiner* — Laura Martin
*Assistant Examiner* — Samir M Shah
(74) *Attorney, Agent, or Firm* — Finnegan, Henderson, Farabow, Garrett & Dunner, L.L.P.

(57) ABSTRACT

According to an embodiment, a pressure sensor includes a substrate, a support part, a flexible membrane part, and a magnetoresistive element. The support part is adhered on the substrate by using a first adhesive material with a first Young's modulus and a second adhesive material with a second Young's modulus different from the first Young's modulus. The membrane part is supported by the support part. The magnetoresistive element is provided on the membrane part, and includes a first magnetic layer, a second magnetic layer, and a spacer layer provided between the first magnetic layer and the second magnetic layer.

10 Claims, 7 Drawing Sheets

(51) Int. Cl.
*A61B 5/021* (2006.01)
*A61B 5/00* (2006.01)
*A61B 5/05* (2006.01)
*G01L 9/00* (2006.01)
*G01L 1/12* (2006.01)

(52) U.S. Cl.
CPC .......... *A61B 5/6898* (2013.01); *A61B 5/7475* (2013.01); *G01L 1/125* (2013.01); *G01L 9/007* (2013.01); *A61B 2562/0204* (2013.01); *A61B 2562/028* (2013.01); *A61B 2562/0247* (2013.01)

(56) References Cited

U.S. PATENT DOCUMENTS

| | | | | |
|---|---|---|---|---|
| 5,604,363 | A * | 2/1997 | Ichihashi | G01L 19/147 257/274 |
| 5,721,446 | A * | 2/1998 | Kobayashi | G01L 19/147 257/417 |
| 6,169,316 | B1 * | 1/2001 | Sakai | G01L 19/146 257/417 |
| 6,507,187 | B1 * | 1/2003 | Olivas | G01B 7/24 324/207.21 |
| 6,551,853 | B2 * | 4/2003 | Toyoda | H01L 29/84 257/E29.324 |
| 6,595,065 | B2 * | 7/2003 | Tanizawa | G01L 9/0055 73/720 |
| 6,925,885 | B2 * | 8/2005 | Ishio | G01L 19/143 73/715 |
| 7,024,937 | B2 * | 4/2006 | James | G01L 19/003 73/756 |
| 7,490,522 | B2 * | 2/2009 | Ruehrig | G01L 1/12 73/862.335 |
| 8,373,240 | B2 * | 2/2013 | Elian | G01L 19/141 257/415 |
| 9,366,593 | B2 * | 6/2016 | Vaupel | B81B 7/0048 |
| 2003/0079549 | A1 * | 5/2003 | Lokhorst | G01L 1/205 73/754 |
| 2007/0186666 | A1 * | 8/2007 | Ruehrig | G01L 9/16 73/779 |
| 2008/0094059 | A1 | 4/2008 | Sasaki et al. | |
| 2011/0227178 | A1 * | 9/2011 | Kazama | G01B 7/16 257/417 |
| 2012/0055257 | A1 * | 3/2012 | Shaw-Klein | H01L 41/081 73/780 |
| 2014/0069200 | A1 * | 3/2014 | Yuasa | G01L 9/16 73/725 |
| 2014/0369530 | A1 | 12/2014 | Fuji et al. | |
| 2015/0330854 | A1 * | 11/2015 | Tsushima | G01L 13/026 73/717 |

FOREIGN PATENT DOCUMENTS

| | | |
|---|---|---|
| JP | 2011-247897 | 12/2011 |
| JP | 4894669 | 1/2012 |
| JP | 4997875 | 5/2012 |
| JP | 2014-240824 | 12/2014 |
| TW | 201323845 A1 | 6/2013 |

OTHER PUBLICATIONS

Taiwanese Office Acton dated Mar. 22, 2016 (10 pages total) for Taiwan Application No. 104116487.

Lv, Haojie et al., "A Touch Mode Capacitive Pressure Sensor with Long Linear Range and High Sensitivity," *Proceedings of the 3rd IEEE Int. Conf. on Nano/Micro Engineered and Molecular Systems*, pp. 796-800 (2008).

* cited by examiner

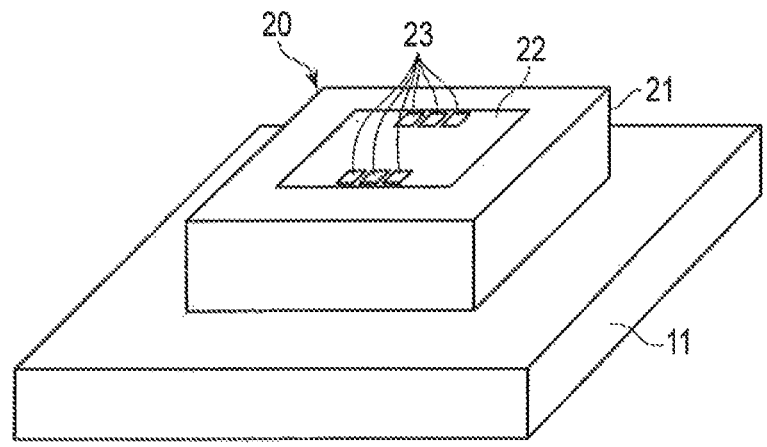
F I G. 1
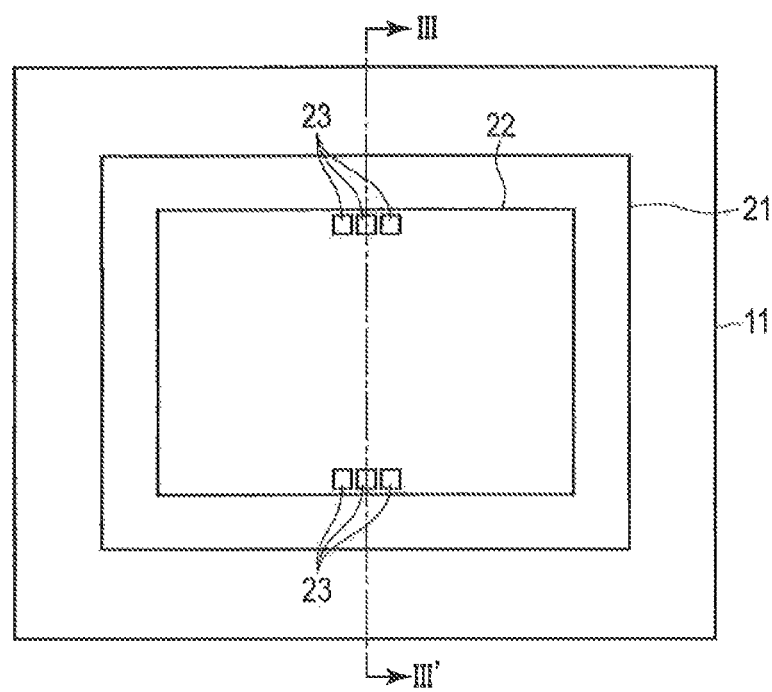
F I G. 2

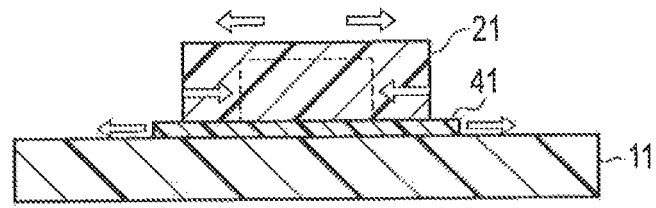
F I G. 10
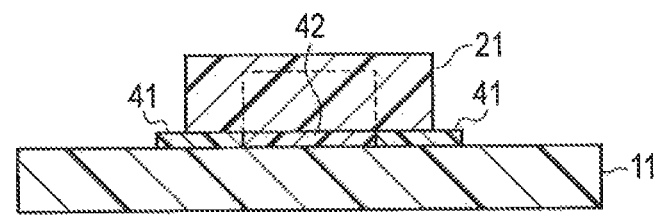
F I G. 11
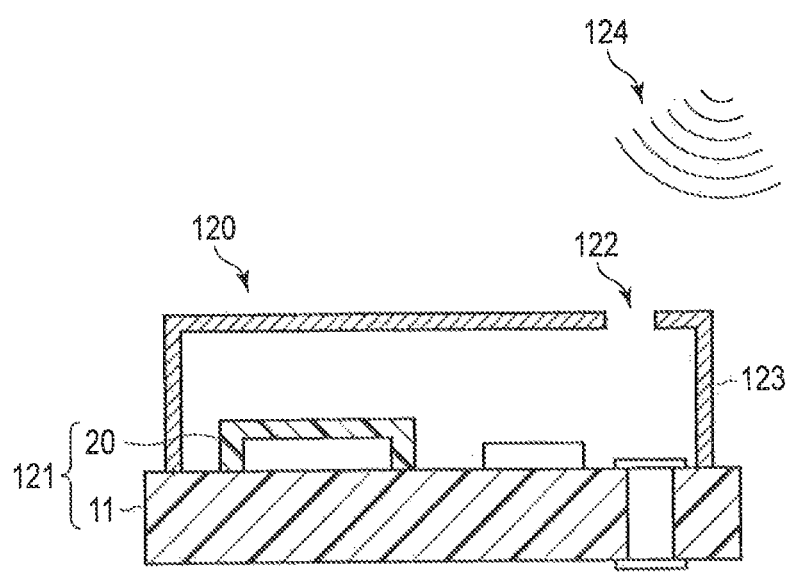
F I G. 12

PRESSURE SENSOR, MICROPHONE, ULTRASONIC SENSOR, BLOOD PRESSURE SENSOR, AND TOUCH PANEL

CROSS-REFERENCE TO RELATED APPLICATIONS

This application is based upon and claims the benefit of priority from Japanese Patent Application No. 2014-108502, filed May 26, 2014, the entire contents of which are incorporated herein by reference.

FIELD

Embodiments described herein relate generally to a pressure sensor, microphone, ultrasonic sensor, blood pressure sensor, and touch panel.

BACKGROUND

Pressure sensors based on the MEMS (Micro Electro Mechanical Systems) technique include a piezoelectric sensor, piezoresistive sensor, capacitance sensor, and the like. On the other hand, a pressure sensor using the spin technique whose sensing principle is different from that of the above-described pressure sensors has been proposed. In the pressure sensor using the spin technique, a spin valve magnetostrictive element (also called a magnetoresistive (MR) element) detects a resistance change corresponding to an anisotropic strain caused by an external pressure. Demands have arisen for increasing the sensitivity of the pressure sensor using the spin technique.

BRIEF DESCRIPTION OF THE DRAWINGS

FIG. 1 is a perspective view showing a pressure sensor according to the first embodiment;

FIG. 2 is a plan view showing the pressure sensor according to the first embodiment;

FIG. 10 is a sectional view of the pressure sensor taken along a line X-X' shown in FIG. 9;

FIG. 11 is a sectional view of the pressure sensor taken along a line XI-XI' shown in FIG. 9;

FIG. 12 is a sectional view showing a microphone according to the third embodiment;

DETAILED DESCRIPTION

Figure 3:
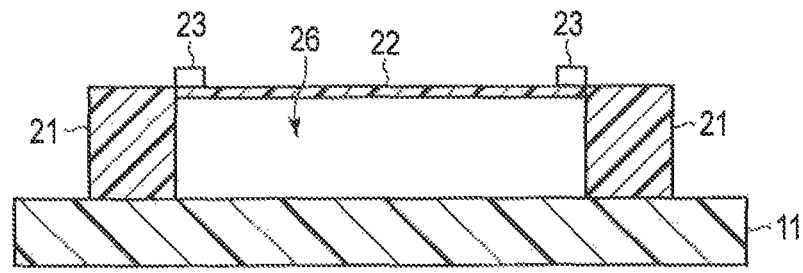
FIG. 3 is a sectional view of the pressure sensor taken along a line III-III' shown in FIG. 2.

According to an embodiment, a pressure sensor includes a substrate, a support part, a flexible membrane part, and a magnetoresistive element. The support part is adhered on the substrate by using a first adhesive material with a first Young's modulus and a second adhesive material with a second Young's modulus different from the first Young's modulus. The membrane part is supported by the support part. The magnetoresistive element is provided on the membrane part, and includes a first magnetic layer, a second magnetic layer, and a spacer layer provided between the first magnetic layer and the second magnetic layer.

Embodiments will be described hereinafter with reference to the accompanying drawings. The embodiments are directed to a pressure sensor based on the MEMS (Micro Electro Mechanical Systems) technique, and a microphone, ultrasonic sensor, blood pressure sensor, and touch panel using the pressure sensor. Note that the drawings are schematic or conceptual, so the relationship between the thickness and width of each part, the size ratio between parts, and the like are not necessarily the same as real ones. Also, the dimension or ratio of even the same part may change from one drawing to another. In the following embodiments, the same reference numerals denote the same elements, and a repetitive explanation thereof will be omitted.

First Embodiment

FIGS. 1 and 2 are respectively a perspective view and plan view schematically showing a pressure sensor according to the first embodiment. FIG. 3 schematically shows a cross-section of the pressure sensor obtained along a line III-III' shown in FIG. 2. FIGS. 1, 2, and 3 do not illustrate insulating parts, conductive parts, and the like for the sake of simplicity. The pressure sensor shown in FIG. 1 includes a resin substrate 11, and a MEMS chip 20 mounted on the resin substrate 11. The MEMS chip 20 is adhered and fixed on the resin substrate 11 by using an adhesive material (also called a die bonding material) such as a thermosetting resin.

The MEMS chip 20 includes a support part 21 provided on the resin substrate 11, a diaphragm 22 corresponding to a flexible membrane part supported by the support part 21, and magnetoresistive elements 23 provided on the diaphragm 22. When an external pressure is applied, the diaphragm 22 bends or warps and applies a strain to the magnetoresistive elements 23 formed on it. The external pressure may be a pressure caused by, for example, pressing, a sound wave, or an ultrasonic wave. The electrical resistance of the magnetoresistive element 23 changes in accordance with the magnitude of the strain having occurred on the magnetoresistive element 23. The pressure sensor according to this embodiment can sense the external pressure by detecting this change in electrical resistance.

Note that FIG. 1 shows an example in which six magnetoresistive elements 23 are provided, but the number of magnetoresistive elements 23 need not be six, and may also be one, two to five, or seven or more.

The support part 21 is, for example, a silicon (Si) substrate. The support part 21 is formed into, for example, a square cylindrical shape having a cavity 26 shown in FIG. 3. The cavity 26 opens to two surfaces of the support part 21 opposing each other. One of these two surfaces is a surface to be adhered to the resin substrate 11, and the diaphragm 22 is fixed to the other of these two surfaces. The cavity 26 is sealed by the resin substrate 11 and the diaphragm 22. The cavity 26 can be filled with a gas such as air or an inert gas, or, on the contrary, can be evacuated. The cavity 26 may also be filled with a liquid. Note that the shape of the support part 21 is not limited to the above-described shape and may also be any arbitrary shape, as long as the support part 21 can support the diaphragm 22 so that the diaphragm 22 can bend when an external pressure is applied.

The diaphragm 22 is formed by a thin film such as an amorphous silicon (a-Si) film, silicon oxide ($SiO_x$) film, aluminum oxide ($AlO_x$) film, or silicon nitride (SiN) film. The thin film forming the diaphragm 22 is sometimes continuously formed outside the part which bends due to an external pressure. In this embodiment, that part of the thin film, which bends due to an external pressure, will be called a diaphragm (membrane part). The membrane part is a thin-film region processed to be thin.

In this embodiment, as shown in FIG. 2, the diaphragm 22 is formed into a rectangle, and three magnetoresistive elements 23 are arranged in each of the two end parts along the long sides. A direction parallel to the short sides of the diaphragm 22 will be called a widthwise direction, and a direction parallel to the long sides of the diaphragm 22 will be called a longitudinal direction. The edges (the two long sides and two short sides) of the diaphragm 22 are fixed to the support part 21. The change in electrical resistance of the magnetoresistive element 23 increases as a strain (more specifically, an anisotropic strain as a difference between a maximum principal strain and a minimum principal strain) having occurred on the magnetoresistive element 23 increases. Therefore, to increase the sensitivity of the pressure sensor, the magnetoresistive elements 23 are arranged on the diaphragm 22 so as to generate a large strain with respect to an external pressure. In the rectangular diaphragm 22, an anisotropic strain larger than that occurring in the end part along the short side or in the central part occurs in the end part along the long side. Accordingly, the magnetoresistive elements 23 are preferably arranged in the end parts along the long sides of the diaphragm 22.

A step of mounting the MEMS chip 20 on the resin substrate 11 has a large influence on a strain occurring on the diaphragm 22. In this embodiment, the MEMS chip 20 is mounted on the resin substrate 11 so as to apply an anisotropic strain to the diaphragm 22. This makes high-sensitivity sensing possible even for a low pressure as will be explained next.

Figure 4:
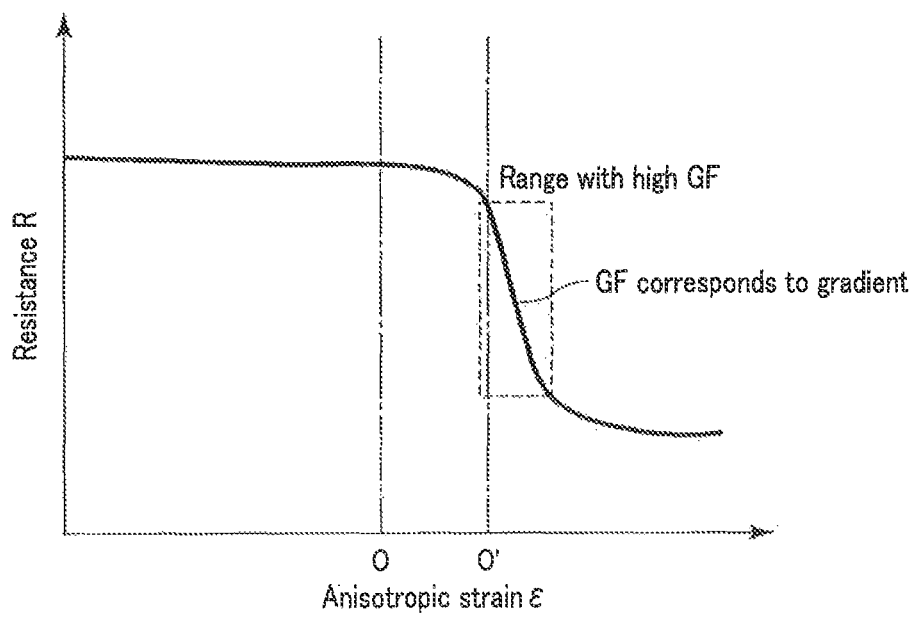
FIG. 4 is a graph showing the relationship between an anisotropic strain ε and resistance R in a magnetoresistive element.

FIG. 4 shows an example of the relationship between an anisotropic strain ε and electrical resistance R in a magnetoresistive element. In FIG. 4, the transverse axis shows the anisotropic strain ε, and the vertical axis shows the resistance R. The sensitivity of the magnetoresistive element increases as a gauge factor GF indicating the ratio of the resistance change rate to the anisotropic strain increases. The gauge factor GF is represented by equation (1) below, and corresponds to the gradient on the graph shown in FIG. 4.

$$GF = \frac{\frac{\Delta R}{R}}{\Delta \varepsilon} \quad (1)$$

where $\Delta R/R$ represents the resistance change rate, and $\Delta \varepsilon$ represents the change in anisotropic strain. The broken lines in FIG. 4 indicate a range within which the gauge factor GF is high. Within this range, high-sensitivity sensing can be performed even for a very small pressure fluctuation.

A point O on the transverse axis indicates an anisotropic strain occurring in a magnetoresistive element according to a comparative example in the initial state in which no external pressure is applied. In this magnetoresistive element according to the comparative example, the change in electrical resistance is small when a low external pressure is applied. That is, the sensitivity is low for a low external pressure. A point O' on the transverse axis indicates an anisotropic strain occurring in the magnetoresistive element 23 according to this embodiment in the initial state in which no external pressure is applied. In this embodiment, an anisotropic strain is added beforehand when mounting the MEMS chip 20, so the anisotropic strain in the initial state of the magnetoresistive element 23 is larger than that of the magnetoresistive element according to the comparative example. Even when a low external pressure is applied, therefore, a large electrical resistance change is obtained in the magnetoresistive element 23. This makes high-sensitivity sensing feasible even for a low external pressure.

An example of the method of mounting the MEMS chip 20 on the resin substrate 11 according to this embodiment will be explained below with reference to FIGS. 5, 6, and 7.

Figure 5:
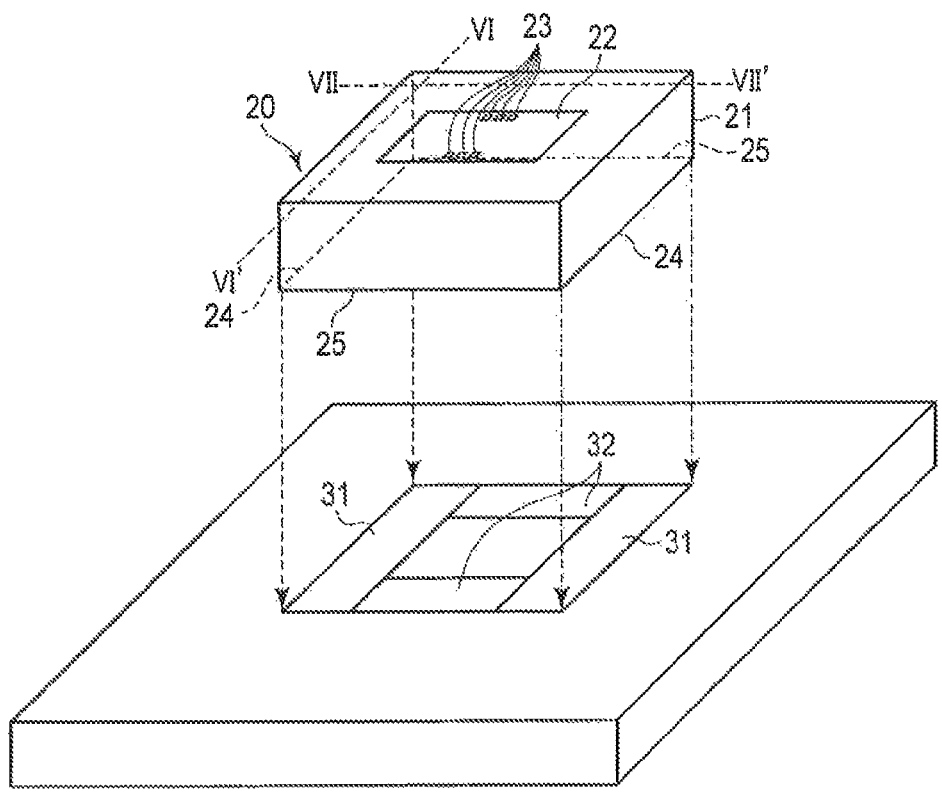
FIG. 5 is an exploded perspective view showing the pressure sensor according to the first embodiment.

FIG. 5 shows a state in which the pressure sensor according to this embodiment is exploded. FIG. 6 shows a cross-section of the pressure sensor obtained along a line VI-VI' shown in FIG. 5. FIG. 7 shows a cross-section of the pressure sensor obtained along a line VII-VII' shown in FIG. 5. As shown in FIG. 5, the MEMS chip 20 is adhered on the resin substrate 11 by using first and second adhesive materials 31 and 32 having different Young's moduli. The second adhesive material 32 has a Young's modulus lower than that of the first adhesive material 31. The first and second adhesive materials 31 and 32 are so arranged that the widthwise-direction component of a strain added to the diaphragm 22 when mounting the MEMS chip 20 becomes larger than the longitudinal-direction component of the strain. Specifically, the first adhesive material 31 is applied to two regions (first regions) of the adhesion surface of the support part 21, which correspond to the two short sides of the diaphragm 22. The first regions extend along two sides 24 parallel to the widthwise direction of the diaphragm 22. The second adhesive materials 32 are applied to those regions (second regions) of the adhesion surface, which are positioned between the first regions. The second regions are formed along two sides 25 parallel to the longitudinal direction of the diaphragm 22.

Figure 6:
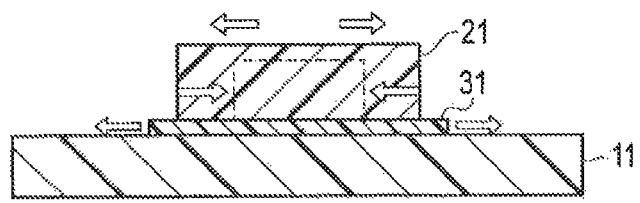
FIG. 6 is a sectional view of the pressure sensor taken along a line VI-VI' shown in FIG. 5.
Figure 7:
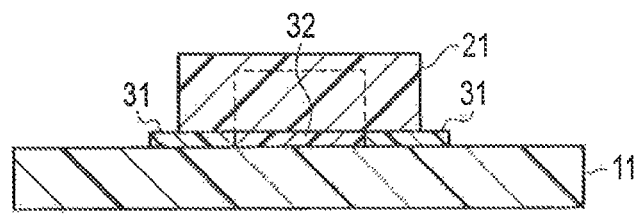
FIG. 7 is a sectional view of the pressure sensor taken along a line VII-VII' shown in FIG. 5.

As shown in FIG. 6, the first adhesive material 31 shrinks during the process of hardening, and generates a tensile residual stress in the widthwise direction of the diaphragm 22. Consequently, a tensile membrane stress occurs on the diaphragm 22 in the widthwise direction thereof. On the other hand, as shown in FIG. 7, no large tensile residual stress occurs in the longitudinal direction of the diaphragm 22. Accordingly, no large tensile membrane stress occurs on the diaphragm 22 in the longitudinal direction thereof. Thus, an anisotropic strain is added to the diaphragm 22.

In this embodiment, an appropriate anisotropic strain can be added to the diaphragm 22 in advance by using the adhesive materials (the first and second adhesive materials 31 and 32) having appropriate Young's moduli. As a consequence, high-sensitivity sensing can be performed even for a low pressure.

Figure 8:
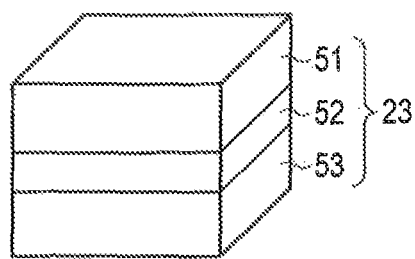
FIG. 8 is a perspective view showing a magnetoresistive element shown in FIG. 1.

FIG. 8 schematically shows one of the six magnetoresistive elements 23 shown in FIG. 1. The remaining five magnetoresistive elements 23 shown in FIG. 1 can have the same structure as that of the magnetoresistive element 23 shown in FIG. 8. FIG. 8 shows a part of the magnetoresistive element 23. As shown in FIG. 8, the magnetoresistive element 23 includes a first magnetic layer 51, a second magnetic layer 53, and an interlayer (also called a spacer layer) 52 arranged between the first magnetic layer 51 and the second magnetic layer 53. At least one of the first magnetic layer 51 and the second magnetic layer 53 is a magnetization free layer in which the magnetization direction is variable. In this embodiment, the first magnetic layer 51 is a magnetization free layer, and the second magnetic layer 53 is a magnetization fixed layer in which the magnetization direction is fixed. The interlayer 52 is a nonmagnetic layer.

An operation by which the magnetoresistive element 23 functions as a strain sensor is based on the application of "the inverse magnetostrictive effect" and "the MR (MagnetoResistance) effect". The inverse magnetostrictive effect is obtained in a ferromagnetic layer to be used as a magnetization free layer. The MR effect appears in a multilayered film in which a magnetization free layer, an interlayer, and a reference layer (e.g., a magnetization fixed layer) are stacked.

The inverse magnetostrictive effect is a phenomenon in which the magnetization direction of a ferromagnetic material changes due to a strain occurring in the ferromagnetic material. That is, when an external strain is applied to the multilayered film of the magnetoresistive element 23, the magnetization direction in the magnetization free layer changes. Consequently, the relative angle between the magnetization directions in the magnetization free layer and the reference layer changes. In this state, the MR effect changes the electrical resistance. The MR effect includes, for example, the GMR (Giant MagnetoResistance) effect or TMR (Tunneling MagnetoResistance) effect. The MR effect appears when an electric current is supplied to the multilayered film. When an electric current is supplied to the multilayered film, a change in relative angle between the magnetization directions can be read as an electrical resistance change. For example, a strain occurs in the multilayered film (the magnetoresistive element 23), the magnetization direction in the magnetization free layer changes due to this strain, and the relative angle between the magnetization directions in the magnetization free layer and reference layer changes. That is, the MR effect appears due to the inverse magnetostrictive effect.

A magnetic layer to be used as the magnetization fixed layer directly contributes to the MR effect. The second magnetic layer 53 as the magnetization fixed layer is made of, for example, a Co—Fe—B alloy. Specifically, a $(Co_xFe_{100-x})_{100-y}B_y$ alloy (x is 0 at. % through 100 at. %, and y is 0 at. % through 30 at. %) can be used as the second magnetic layer 53. As the second magnetic layer 53, another material such as an Fe—Co alloy may also be used.

The interlayer 52 breaks the magnetic bond between the first and second layers 51 and 53. The interlayer 52 is made of, for example, a metal, insulator, or semiconductor. It is possible to use Cu, Au, Ag, etc. as the metal. It is possible to use magnesium oxide (e.g., MgO), aluminum oxide (e.g., $Al_2O_3$), titanium oxide (e.g., TiO), zinc oxide (e.g., ZnO), gallium oxide (Ga—O), etc. as the insulator or semiconductor. It is also possible to use, for example, a CCP (Current-Confined-Path) spacer layer as the interlayer 52. When using the CCP spacer layer as the interlayer 52, it is possible to use, for example, a structure in which a copper (Cu) metal, path is formed in an aluminum oxide ($Al_2O_3$) insulating layer.

A ferromagnetic material is used as the first magnetic layer 51 as the magnetization free layer. Specifically, as the material of the first magnetic layer 51, it is possible to use, for example, an alloy containing at least one of Fe and Co, such as an FeCo alloy or NiFe alloy. Alternatively, as the first magnetic layer 51, it is also possible to use, for example, a Co—Fe—B alloy, an Fe—Co—Si—B alloy, an Fe—Ga alloy having a large magnetostrictive constant λs, an Fe—Co—Ga alloy, a Tb-M-Fe alloy, a Tb-M1-Fe-M2 alloy, an Fe-M3-M-B alloy, Ni, Fe—Al, ferrite, etc.

Note that the shape of the diaphragm 22 is not limited to the rectangle as shown in FIG. 2, and may also be another shape such as a square, circle, or ellipse. Even when the diaphragm 22 is formed into another shape, an appropriate anisotropic strain can be applied to the diaphragm 22 in advance by taking account of the arrangement of the magnetoresistive elements 23, and using adhesive materials having appropriate Young's moduli.

In the pressure sensor according to the first embodiment as described above, the MEMS chip is mounted on the resin substrate by using the two adhesive materials having different Young's moduli so as to apply an anisotropic strain to the diaphragm. This makes it possible to perform high-sensitivity sensing even for a low external pressure, thereby achieving a high sensitivity.

Second Embodiment

In the second embodiment, a MEMS chip is adhered on a substrate by using adhesive materials having different coefficients of thermal expansion (CTE). In the second embodiment, parts different from the first embodiment will be explained, and an explanation of the same parts as those of the first embodiment will be omitted as needed.

Figure 9:
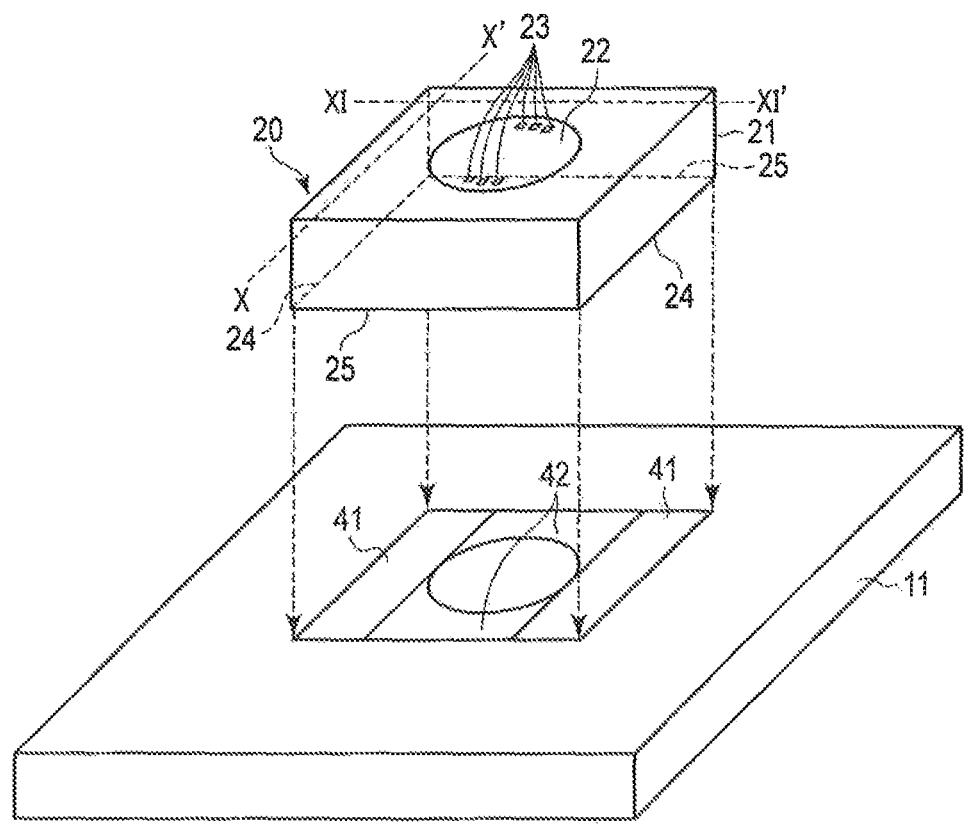
FIG. 9 is an exploded perspective view showing a pressure sensor according to the second embodiment.

FIG. 9 schematically shows a pressure sensor according to the second embodiment in a partially exploded state. FIG. 10 schematically shows a cross-section of the pressure sensor obtained along a line X-X' shown in FIG. 9. FIG. 11 shows a cross-section of the pressure sensor obtained along a line XI-XI' shown in FIG. 9. FIGS. 9, 10, and 11 do not illustrate insulating parts, conductive parts, and the like for the sake of simplicity.

The pressure sensor shown in FIG. 9 includes a resin substrate 11, and a MEMS chip 20 mounted on the resin substrate 11. The MEMS chip 20 includes a support part 21 formed on the resin substrate 11, a flexible diaphragm 22 supported by the support part 21, and at least one magnetoresistive element 23 (in this example, six magnetoresistive elements 23) formed on the diaphragm 22. In this embodiment, the diaphragm 22 is formed into a circular shape, and the magnetoresistive elements 23 are arranged along the periphery of the diaphragm 22. Specifically, three magnetoresistive elements are arranged in each of two end parts opposing each other around the center of the diaphragm 22.

The MEMS chip 20 is adhered on the resin substrate 11 by using first and second adhesive materials 41 and 42 having different coefficients of thermal expansion. The coefficient of thermal expansion of the second adhesive material 42 is lower than that of the first adhesive material 41, and substantially equal to that of the support part 21. The first and second adhesive materials 41 and 42 are so arranged that the first-direction component of a strain added to the diaphragm 22 when mounting the MEMS chip 20 becomes larger than the second-direction component of the strain. The first direction is perpendicular to the second direction. Specifically, the first adhesive material 41 is applied to two regions (first regions) of the adhesion surface of the support part 21, which extend along two sides 24 parallel to the first direction. The dimension of the first region in the first direction is longer than that of the first region in the second direction. The second adhesive materials 42 are applied to those regions (second regions) of the adhesion surface, which are positioned between the first regions. The second regions are formed along two sides 25 parallel to the second direction. The magnetoresistive elements 23 are positioned in the first direction when viewed from the center of the diaphragm 22.

As shown in FIG. 10, the first adhesive material 41 shrinks during the process of hardening, and generates a tensile residual stress in the first direction. Consequently, a tensile membrane stress occurs on the diaphragm 22 in the first direction. On the other hand, as shown in FIG. 11, no large tensile residual stress occurs in the second direction. Accordingly, no large tensile membrane stress occurs on the diaphragm 22 in the second direction. Thus, an anisotropic strain is added to the diaphragm 22.

In this embodiment, an anisotropic strain can be added to the diaphragm 22 in advance by using the adhesive materials (the first and second adhesive materials 41 and 42) having appropriate coefficients of thermal expansion. As a consequence, high-sensitivity sensing can be performed even for a low pressure.

Note that the shape of the diaphragm 22 is not limited to the circle as shown in FIG. 9, and may also be another shape such as a rectangle, square, or ellipse. Even when the diaphragm 22 is formed into another shape, an appropriate anisotropic strain can be applied to the diaphragm 22 in advance by taking account of the arrangement of the magnetoresistive elements 23, and using adhesive materials having appropriate coefficients of thermal expansion.

In the pressure sensor according to the second embodiment as described above, the MEMS chip is mounted on the resin substrate by using the two adhesive materials having different coefficients of thermal expansion so as to apply an anisotropic strain to the diaphragm. This makes it possible to perform high-sensitivity sensing even for a low external pressure, thereby achieving a high sensitivity.

Third Embodiment

FIG. 12 schematically shows a microphone 120 according to the third embodiment. The microphone 120 includes a pressure sensor 121. The pressure sensor 121 can be one of the pressure sensors explained in the first and second embodiments, or a modification thereof. The pressure sensor 121 of this embodiment is the pressure sensor according to the first embodiment.

The pressure sensor 121 includes a resin substrate 11, and a MEMS chip 20 mounted on the resin substrate 11. The resin substrate 11 includes a circuit such as an amplifier. A cover 123 is formed on the resin substrate 11 so as to cover the MEMS chip 20. An opening 122 is formed in the cover 123. A sound wave 124 propagates inside the cover 123 through the opening 122.

The microphone 120 is sensitive to the sound pressure of the sound wave 124. The microphone 120 having high sensitivity to frequencies in a broad range can be obtained by using a high-sensitivity pressure sensor. As a method of reducing a compressive stress occurring on a diaphragm, a method of forming a slit or through hole in the diaphragm is possible. When using a pressure sensor in a microphone, however, the slit or through hole causes roll-off in a low-frequency region by a wraparound of sound waves. In the pressure sensor 121 of this embodiment, this roll-off by a wraparound of sound waves does not occur, so the sensitivity is high in a low-frequency region as well.

Note that the sound wave 124 is not limited to an audible-range signal and may also be an ultrasonic wave. When designing the diaphragm 22 so that the resonance frequency of the diaphragm 22 is the frequency band of an ultrasonic wave, the microphone 120 can function as an ultrasonic sensor. More preferably, the opening 122 is formed immediately above the diaphragm (not shown in FIG. 12) of the pressure sensor 121, or formed in the resin substrate 11 immediately below the diaphragm, because the ability of a sound wave to travel straight increases when it is an ultrasonic wave. Furthermore, a dust-proof mesh is desirably formed in the opening 122.

Figure 13:
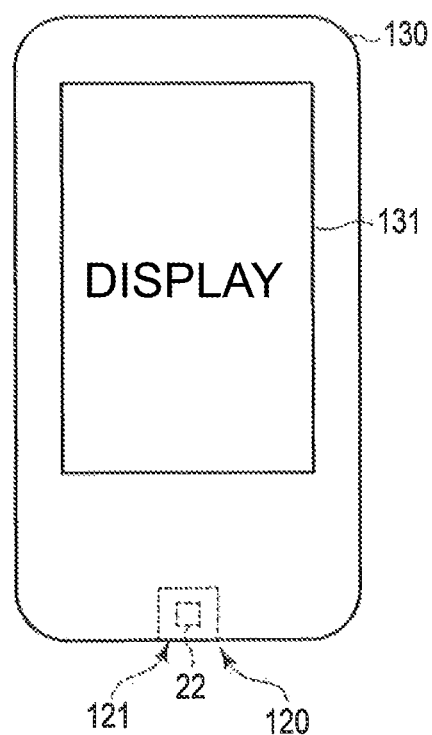
FIG. 13 is a front view showing a personal digital assistance including the microphone shown in FIG. 12.

FIG. 13 schematically shows an example in which the microphone 120 is applied to a personal digital assistance 130. As shown in FIG. 13, the microphone 120 is provided on the end part of the personal digital assistance 130. For example, the microphone 120 is arranged so that the diaphragm 22 of the pressure sensor 121 is practically parallel to the surface of the personal digital assistance 130, on which a display 131 is formed. Note that the position of the diaphragm 22 is not limited to the example shown in FIG. 13, and can be changed as needed.

Note also that the microphone 120 can be applied not only to the personal digital assistance 130 as shown in FIG. 13, but also to an IC recorder, pin microphone, or the like.

Fourth Embodiment

Figure 14:
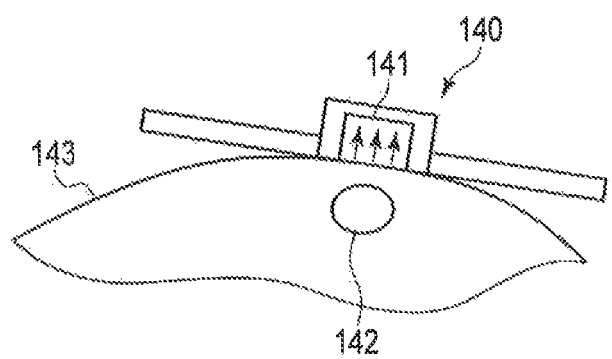
FIG. 14 is a sectional view showing a blood pressure sensor according to the fourth embodiment.

FIG. 14 schematically shows a blood pressure sensor 140 according to the fourth embodiment. The blood pressure sensor 140 shown in FIG. 14 measures a person's blood pressure, and includes a pressure sensor 141. The pressure sensor 141 can be one of the pressure sensors explained in the first and second embodiments, or a modification thereof. The pressure sensor 141 of this embodiment is the pressure sensor according to the first embodiment, and is capable of high-sensitivity pressure sensing with a small size.

The blood pressure sensor 140 can continuously perform blood pressure measurement by pressing the pressure sensor 141 against a skin 143 on an artery 142. This embodiment provides the blood pressure sensor 140 having high sensitivity.

Fifth Embodiment

Figure 15:
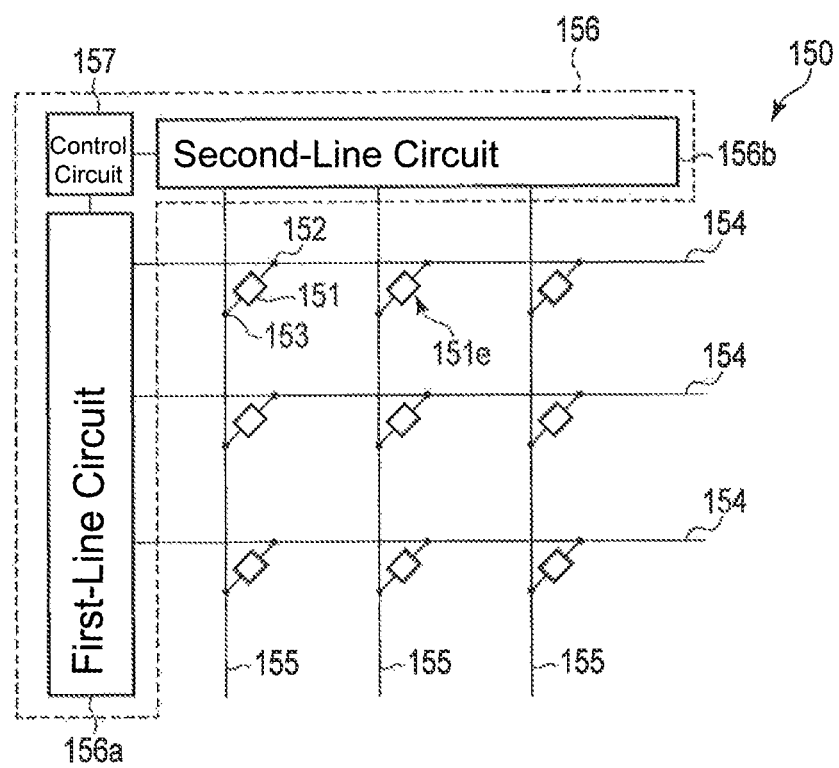
FIG. 15 is a block diagram showing a touch panel according to the fifth embodiment.

FIG. 15 schematically shows a touch panel 150 according to the fifth embodiment. As shown in FIG. 15, the touch panel 150 includes first lines 154, second lines 155, pressure sensors 151, and a controller 156. Each of the pressure sensors 151 can be one of the pressure sensors according to the first and second embodiments, or a modification thereof. The pressure sensors 151 are mounted inside or outside a display.

The first lines 154 are arranged along a first direction. Each of the first lines 154 runs along a second direction perpendicular to the first direction. The second lines 155 are arranged along the second direction. Each of the second lines 155 runs along the first direction.

Each of the pressure sensors 151 is formed in each of the intersections of the first lines 154 and the second lines 155. Each pressure sensor 151 functions as a detection element 151e for detection. The intersection herein mentioned includes a position where the first and second lines 154 and 155 intersect, and a peripheral region thereof.

An end 152 of each of the pressure sensors 151 is connected to a corresponding one of the first lines 154. An end 153 of each of the pressure sensors 151 is connected to a corresponding one of the second lines 155.

The controller 156 is connected to the first lines 154 and the second lines 155. The controller 156 includes a first-line circuit 156a connected to the first lines 154, a second-line circuit 156b connected to the second lines 155, and a control circuit 157 connected the first-line circuit 156a and second-line circuit 156b.

The pressure sensor 151 is capable of high-sensitivity pressure sensing with a small size. This makes it possible to implement a high-definition touch panel.

The pressure sensors according to the first and second embodiments are not limited to the above-mentioned applications, and are also applicable to various pressure sensor devices such as an atmospheric pressure sensor and tire inflation pressure sensor.

According to the embodiments, there are provided a high-sensitivity pressure sensor, microphone, ultrasonic sensor, blood pressure sensor, and touch panel.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A pressure sensor comprising:
    a membrane comprising a peripheral edge, the peripheral edge including a first edge portion, a second edge portion, a third edge portion and a fourth edge portion, the first edge portion being opposed to the second edge portion, the third edge portion being opposed to the fourth edge portion;
    a support member supporting a part of the peripheral edge of the membrane;
    a first adhesive member comprising a first adhesive material with a first Young's modulus;
    a second adhesive member comprising the first adhesive material, the first adhesive member and the second adhesive member being arranged in a first direction;
    a third adhesive member comprising a second adhesive material with a second Young's modulus;
    a fourth adhesive member comprising the second adhesive material, the third adhesive member and the fourth adhesive member being arranged in a second direction, the second direction intersecting with the first direction;
    a substrate, the first adhesive member being provided between the first edge portion and the substrate, the second adhesive member being provided between the second edge portion and the substrate, the third adhesive member being provided between the third edge portion and the substrate, the fourth adhesive member being provided between the fourth edge portion and the substrate; and
    a magnetoresistive element provided on the membrane part, the magnetoresistive element including a first magnetic layer, a second magnetic layer, and a spacer layer provided between the first magnetic layer and the second magnetic layer.

2. The sensor according to claim 1, wherein a length of the first edge portion and the second edge portion is shorter than a length of the third edge portion and the fourth edge portion, respectively, and the second Young's modulus is lower than the first Young's modulus.

3. The sensor according to claim 1, wherein the magnetoresistive element is provided on the third edge portion.

4. The sensor according to claim 3, comprising a plurality of magnetoresistive elements provided on the third edge portion.

5. A pressure sensor comprising:
    a membrane comprising a peripheral edge, the peripheral edge including a first edge portion, a second edge portion, a third edge portion and a fourth edge portion, the first edge portion being opposed to the second edge portion, the third edge portion being opposed to the fourth edge portion;
    a support member supporting a part of the peripheral edge of the membrane;
    a first adhesive member comprising a first adhesive material with a first coefficient of thermal expansion;
    a second adhesive member comprising the first adhesive material, the first adhesive member and the second adhesive member being arranged in a first direction;
    a third adhesive member comprising a second adhesive material with a second coefficient of thermal expansion;
    a fourth adhesive member comprising the second adhesive material, the third adhesive member and the fourth adhesive member being arranged in a second direction, the second direction intersecting with the first direction;
    a substrate, the first adhesive member being provided between the first edge portion and the substrate, the second adhesive member being provided between the second edge portion and the substrate, the third adhesive member being provided between the third edge portion and the substrate, the fourth adhesive member being provided between the fourth edge portion and the substrate; and
    a magnetoresistive element provided on the membrane, the magnetoresistive element including a first magnetic layer, a second magnetic layer, and a spacer layer provided between the first magnetic layer and the second magnetic layer.

6. The sensor according to claim 5, wherein a length of the first edge portion and the second edge portion is shorter than a length of the third edge portion and the fourth edge portion, respectively, and the second coefficient of thermal expansion is lower than the first coefficient of thermal expansion.

7. The sensor according to claim 5, wherein the magnetoresistive element is provided on the third edge portion.

8. The sensor according to claim 7, comprising a plurality of magnetoresistive elements provided on the third edge portion.

9. A pressure sensor comprising:
    a membrane comprising a peripheral edge, the peripheral edge including a first edge portion, a second edge portion, a third edge portion and a fourth edge portion, the first edge portion being opposed to the second edge portion, the third edge portion being opposed to the fourth edge portion;
    a support member supporting a part of the peripheral edge of the membrane;
    a first adhesive member and a second adhesive member comprising a first adhesive material, the first adhesive member and the second adhesive member being arranged in a first direction;
    a third adhesive member and a fourth adhesive member comprising a second adhesive material, the third adhesive member and the fourth adhesive member being arranged in a second direction, the second direction intersecting with the first direction;

a substrate, the first adhesive member being provided between the first edge portion and the substrate, the second adhesive member being provided between the second edge portion and the substrate, the third adhesive member being provided between the third edge portion and the substrate, the fourth adhesive member being provided between the fourth edge portion and the substrate; and a magnetoresistive element provided on the membrane, the magnetoresistive element including a first magnetic layer, a second magnetic layer, and a spacer layer provided between the first magnetic layer and the second magnetic layer.

10. The sensor according to claim 9, wherein a length of the first edge portion and the second edge portion is shorter than a length of the third edge portion and the fourth edge portion, respectively, and the magnetoresistive element is provided on the third edge portion.

* * * * *